US00PP18977P2

(12) United States Plant Patent
Stephens

(10) Patent No.: US PP18,977 P2
(45) Date of Patent: Jun. 24, 2008

(54) ***LOROPETALUM* PLANT NAMED 'NCI002'**

(50) Latin Name: *Loropetalum chinense*
Varietal Denomination: NCI002

(76) Inventor: Carroll Theodore Stephens, 20 Stephens Estate, North Augusta, SC (US) 29860

( * ) Notice: Subject to any disclaimer, the term of this patent is extended or adjusted under 35 U.S.C. 154(b) by 134 days.

(21) Appl. No.: 11/501,511

(22) Filed: Aug. 9, 2006

(51) Int. Cl.
*A01H 5/00* (2006.01)

(52) U.S. Cl. ..... Plt./226
(58) Field of Classification Search ..... Plt./226
See application file for complete search history.

*Primary Examiner*—Kent L Bell
(74) *Attorney, Agent, or Firm*—Jondle & Associates, P.C.

(57) ABSTRACT

A *Loropetalum chinense* cultivar particularly distinguished by having a densely compact habit, green foliage color, and abundant white flowers is disclosed.

3 Drawing Sheets

Genus and species: *Loropetalum chinense.*
Variety denomination: 'NCI002'.

BACKGROUND OF THE NEW PLANT

The present invention comprises a new and distinct cultivar of *Loropetalum,* botanically known as *Loropetalum chinense,* and hereinafter referred to by the cultivar name 'NCI002'. The new cultivar was discovered as an open-pollinated seedling. It is believed to be a cross between the white blooming *Loropetalum chinense* cultivar 'Hillier' (unpatented) and the pink blooming *Loropetalum chinense* var. rubrum cultivar 'Blush' (unpatented). The seedling was discovered in North Augusta, S.C. in 2001.

The genus *Loropetalum* is included in the family Hamamelidaceae that comprises about 15 genera of shrubs and trees growing in the northern hemisphere. *Loropetalum* comprises one species of evergreen shrub or small tree which possesses desirable ornamental characteristics. *Loropetalum* was first introduced to Europe as an ornamental plant in the 1880s and is believed to have been cultivated in North America since the early 1930s. *Loropetalum chinense*. rubrum is a native of China and was first discovered in 1928 in Hunan Province. It was rediscovered in the late 1980s and subsequently introduced to the United States.

Asexual reproduction of the new cultivar by stem cuttings at North Augusta, S.C. since 2002 has shown that the distinctive characteristics of this new *Loropetalum* are stable and reproduce true to type in successive generations of asexual propagation.

DESCRIPTION OF THE PHOTOGRAPHS

This new *Loropetalum* plant is illustrated by the accompanying photographs which show the plant's form, foliage and flowers. The colors shown are as true as can be reasonably obtained by conventional photographic procedures.

DESCRIPTION OF THE NEW CULTIVAR

Figure 1:
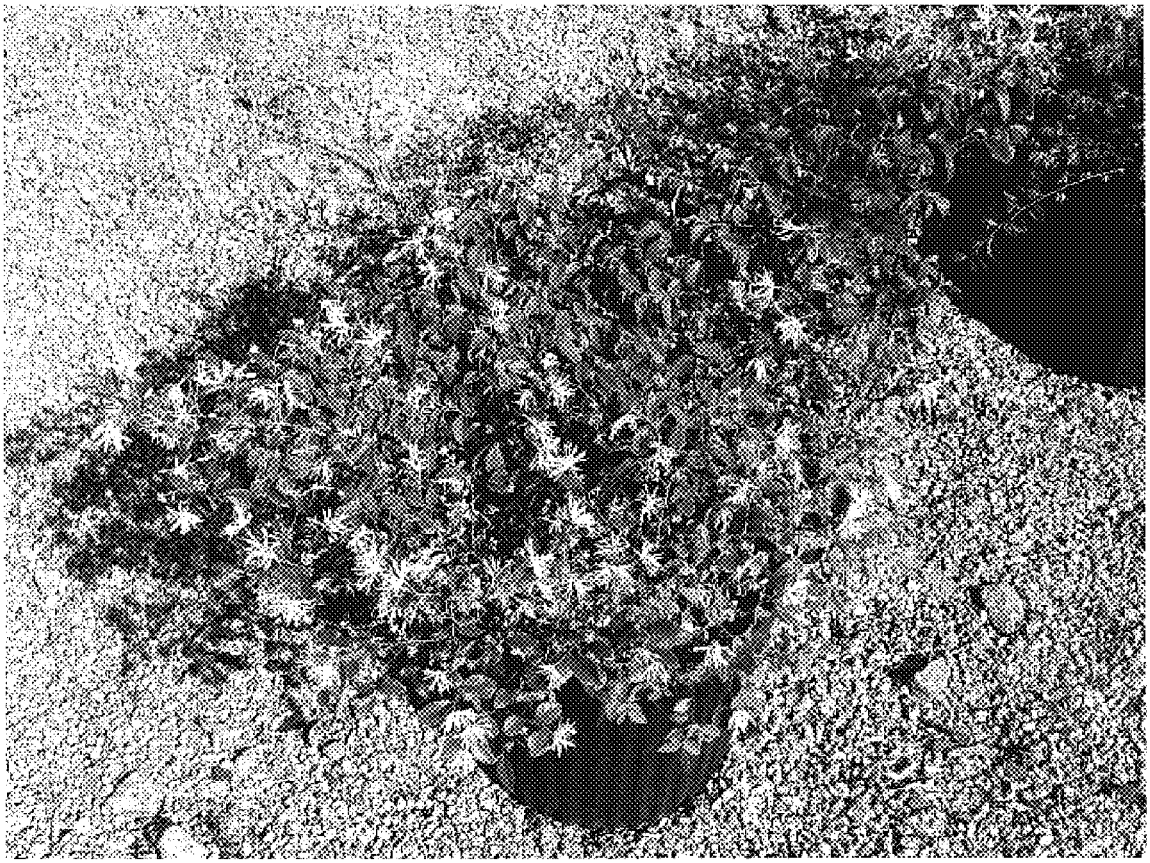
FIG. 1 shows the mature plant's form, foliage and flowers.
Figure 2:
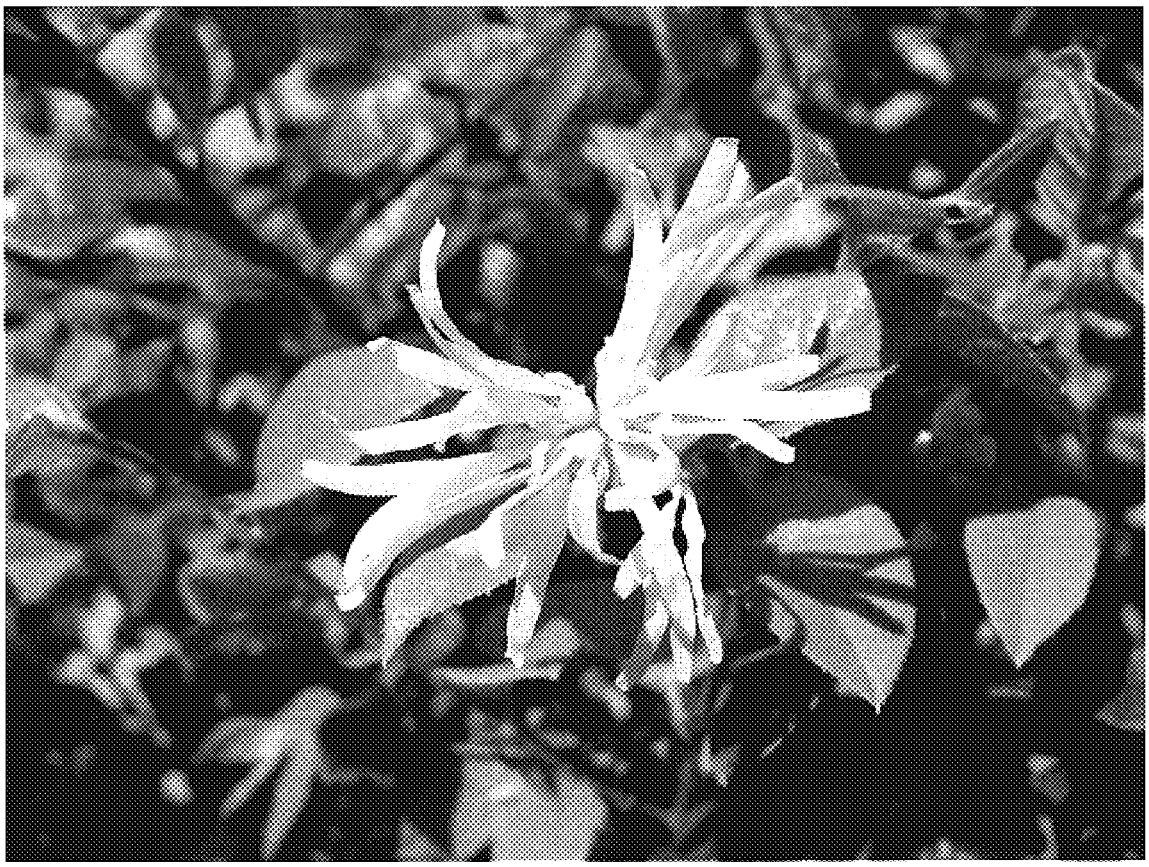
FIG. 2 shows a close-up view of the flower.
Figure 3:
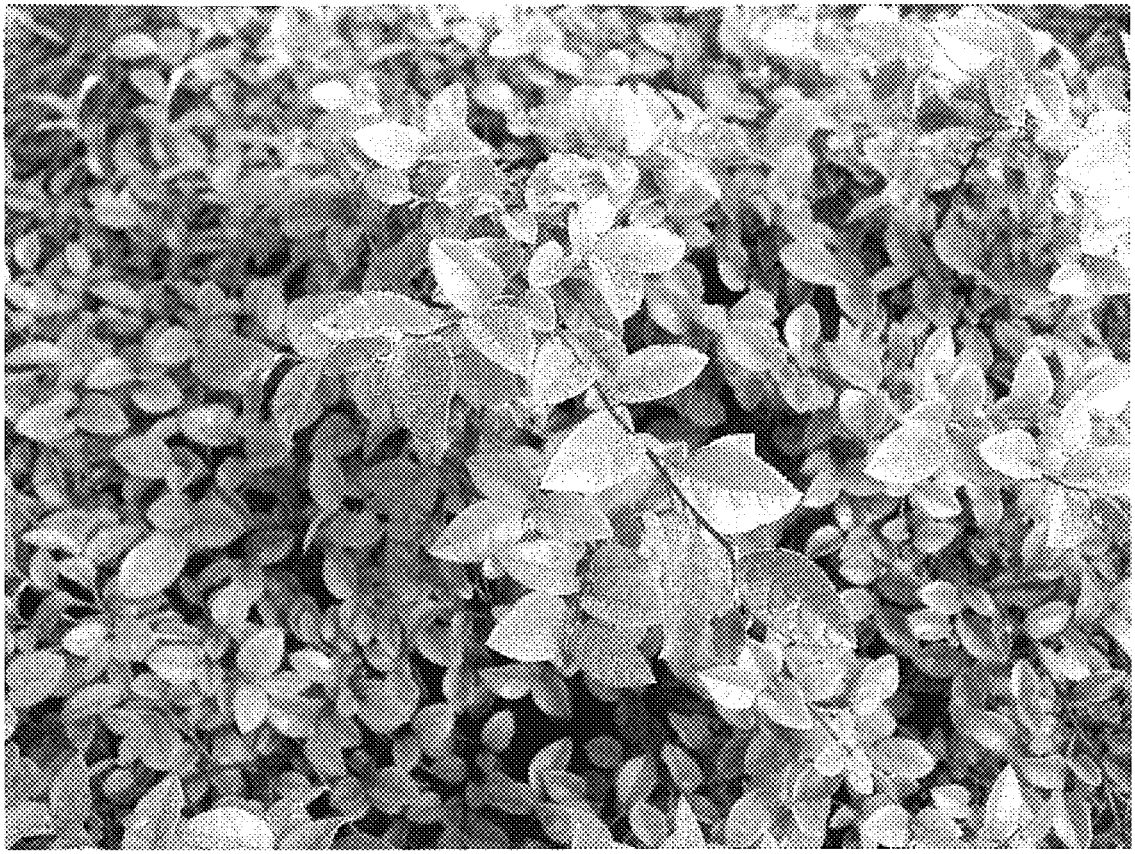
FIG. 3 shows new growth of the foliage.

The following detailed description sets forth the distinctive characteristics of 'NCI002'. The data which define these characteristics were collected from asexual reproductions carried out in Dearing, Ga. The detailed description was taken on 3-year-old plants grown in 3-gallon pots and in the landscape. Color readings were taken in natural light. Observations were made of plants throughout the year in both shade and sun. Color references are to the Colour Chart of The Royal Horticultural Society of London (R.H.S.), 2001 edition.

DETAILED BOTANICAL DESCRIPTION

Classification:
- *Family.*—Hamamelidaceae.
- *Botanical name.*—*Loropetalum chinense.*
- *Common name.*—Chinese fringe flower, Asian witch hazel.

Parentage:
- *Female parent.*—Believed to be the white-flowered *Loropetalum chinense* 'Hillier'.
- *Male parent.*—Believed to be the pink-flowered *Loropetalum chinense* var. rubrum 'Blush'.

Plant description:
- *Type.*—Perennial, evergreen shrub.
- *Form.*—Broad-rounded.
- *Habit.*—Multi-trunk with horizontal and vertical branches, short internodes, and all lateral buds breaking to form a densely compact, broad-rounded shape.
- *Height.*—44.7 cm.
- *Width.*—83.8 cm.

Propagation:
- *Type.*—Vegetative cuttings.
- *Time to initiate roots.*—21 to 28 days at 29 degrees Celsius.
- *Time to produce a rooted young plant.*—60 to 70 days at 29 degrees Celsius.
- *Root description.*—Fibrous, freely branching, light brown in color.

Branches:
- *Habit.*—Planar branches at 45 degree angles to trunks.
- *Lateral branches.*—Number: 45. Length: 34.5 cm. Diameter: 0.4 cm. Internode length: 1.5 cm. Shape:

Round. Color: New growth: RHS 146A (Yellow-Green). First-year growth: RHS N199A (Grey-Brown). Second-year growth: RHS 197A (Greyed-Green). Pubescence: New growth: Heavy. First and second year: Moderate to heavy. Lenticels: Visible on second year and older wood.

Leaves:
- *Arrangement.*—Alternate.
- *Type.*—Simple.
- *Shape.*—Broadly elliptic.
- *Margin.*—Entire.
- *Apex.*—Acute.
- *Base.*—Inequilateral.
- *Length.*—2.4 cm.
- *Width.*—1.4 cm.
- *Texture.*—Upper surface: Matte. Lower surface: Dull.
- *Pubescence.*—Upper surface: Sparse. Lower surface: Moderate.
- *Venation.*—Pinnate.
- *Color.*—Immature leaves: Upper surface: RHS 176B (Greyed-Orange) turning to RHS 146B (Yellow-Green). Lower surface: RHS 148B (Yellow-Green) with a hint of RHS 174A (Greyed-Orange) turning to RHS 148B (Yellow-Green). Mature leaves: Upper surface: RHS 139A (Green). Lower surface: RHS 147B (Yellow-Green).

Petioles:
- *Length.*—0.4 cm.
- *Diameter.*—0.1 cm.
- *Texture.*—Rough, heavily pubescent.
- *Color.*—RHS 148B (Yellow-Green).
- *Stipules.*—Stipule length: 0.4 cm. Stipule width: 0.05 cm. Stipule color: RHS 145B (Yellow-Green).

Inflorescence:
- *Type.*—Umbel, round.
- *Length.*—1.0 cm.
- *Width.*—2.0 cm.
- *Habit.*—Configuration of florets forms an upright, rounded umbel.
- *Number of florets per inflorescence.*—5–6.
- *Flowering period.*—3 to 4 weeks in late March-early April with sporadic blooming throughout the growing season.
- *Lastingness of flowers on the plant.*—5 to 7 days.
- *Fragrance.*—None.

Inflorescence buds:
- *Bud length.*—0.3 cm.
- *Bud width.*—0.2 cm.
- *Bud shape.*—Cuneate-obovate.
- *Bud color.*—RHS 144D (Yellow-Green).

Petals:
- *Arrangement.*—Opposite, four arising from calyx tube at sepal base.
- *Number.*—4.
- *Shape.*—Ribbon or strap-like.
- *Margin.*—Entire.
- *Apex.*—Obcordate.
- *Length.*—1.4 cm.
- *Width.*—0.1 cm.
- *Texture.*—Smooth, matte.
- *Color.*—When opening: RHS 145C (Yellow-Green). When fully opened: RHS 155C (White). Fading to: RHS 155B (White).

Sepals:
- *Arrangement.*—Opposite.
- *Number.*—4.
- *Shape.*—Ovate.
- *Margin.*—Entire.
- *Apex.*—Acute to obtuse, curling outward.
- *Base.*—Fused at base.
- *Length.*—0.32 cm.
- *Width.*—0.24 cm.
- *Texture.*—Matte.
- *Color.*—Immature: RHS 145C (Yellow-Green), both surfaces. Mature: RHS 144D (Yellow-Green), both surfaces.

Calyx and peduncle:
- *Calyx.*—Shape: Urn shaped. Length: 0.4 cm. Width: 0.3 cm. Color: RHS 144D (Yellow-Green).
- *Peduncle.*—Length: 1.0 cm. Width: 1.0 cm. Angle: 25 degrees to the stem. Texture: Heavily pubescent. Color: RHS 144A (Yellow-Green).

Reproductive organs:
- *Stamens.*—Number: 5. Anthers: Shape: Oblong. Length: 0.07 cm. Width: 0.07 cm. Color: RHS 145A (Yellow-Green). Pollen: Quantity: Sparse to Moderate. Color: RHS 155D (White).
- *Pistils.*—Number: 1–2. Length: 0.025 cm.
- *Stigma.*—Shape: Irregular rounded shape with small finger-like projections. Length: 0.025 cm. Diameter: 0.025 cm. Color: RHS 157A (Green-White).
- *Style.*—Length: 0.025 cm. Diameter: 0.025 cm. Color: RHS 157A (Green-White).
- *Ovary.*—Shape: Rounded. Color: RHS 145C (Yellow-Green).

Seeds:
- *Number.*—1.
- *Length.*—0.6 cm.
- *Width.*—0.3 cm.
- *Color.*—RHS 161D (Greyed-Yellow).

Fruit:
- *Type.*—Capsule.
- *Number.*—1–2 per lateral branch.
- *Length.*—0.64 cm.
- *Width.*—0.48 cm.
- *Color.*—RHS 146B (Yellow-Green).
- *Texture.*—Heavily pubescent, dull.
- *Length of ripening.*—60–75 days.

Disease and insect resistance: Typical of species.

COMPARISON WITH KNOWN CULTIVARS

*Loropetalum chinense* 'NCI002' is a distinct variety of *Loropetalum* due to its densely compact habit, green foliage color, and white flower color. Compared to the probable female parent 'Hillier' (unpatented), 'NCI002' has a much more compact growth habit than 'Hillier'. Compared to the probable male parent 'Blush' (unpatented), 'NCI002' has yellow-green immature leaves that mature to green while 'Blush' has burgundy foliage that turns green. In addition, 'NCI002' has white flowers while 'Blush' has pink flowers.

'NCI002' can be compared to the commercial *Loropetalum* variety 'Snowmound' (U.S. Plant Pat. No. 11,766). 'NCI002' has yellow-green new growth with greyed-orange tint, is easier to propagate, and is more vigorous than 'Snowmound'.

I claim:

1. A new and distinct *Loropetalum* plant as shown and described herein.

* * * * *